(12) United States Patent
Yu et al.

(10) Patent No.: US 11,350,873 B2
(45) Date of Patent: Jun. 7, 2022

(54) PORTABLE QUANTIFICATION APPARATUS AND METHOD FOR ASSESSING JOINT ACCESSORY MOVEMENT

(71) Applicant: NATIONAL YANG MING CHIAO TUNG UNIVERSITY, Taipei (TW)

(72) Inventors: Chung-Huang Yu, Taipei (TW); Hsiao-Kuan Wu, Taipei (TW)

(73) Assignee: NATIONAL YANG MING CHIAO TUNG UNIVERSITY, Taipei (TW)

(*) Notice: Subject to any disclaimer, the term of this patent is extended or adjusted under 35 U.S.C. 154(b) by 485 days.

(21) Appl. No.: 15/922,597

(22) Filed: Mar. 15, 2018

(65) Prior Publication Data

US 2018/0199881 A1    Jul. 19, 2018

Related U.S. Application Data

(63) Continuation of application No. 14/615,973, filed on Feb. 6, 2015, now abandoned.

(60) Provisional application No. 61/936,488, filed on Feb. 6, 2014.

(51) Int. Cl.
*A61B 5/00* (2006.01)
*A61B 90/00* (2016.01)
*A61B 5/11* (2006.01)

(52) U.S. Cl.
CPC .......... *A61B 5/4528* (2013.01); *A61B 5/1121* (2013.01); *A61B 90/06* (2016.02); *A61B 5/0051* (2013.01); *A61B 5/7475* (2013.01); *A61B 2090/061* (2016.02); *A61B 2090/064* (2016.02); *A61B 2090/067* (2016.02)

(58) Field of Classification Search
CPC ... A61B 5/4528; A61B 5/4566; A61B 5/1121; A61B 5/0051; A61B 90/06; A61B 2090/061; A61B 2090/064; A61B 2090/067
See application file for complete search history.

(56) References Cited

U.S. PATENT DOCUMENTS

| | | | |
|---|---|---|---|
| 4,762,134 A * | 8/1988 | Gala | A61B 5/1104 600/594 |
| 5,291,901 A * | 3/1994 | Graf | A61B 5/103 600/594 |
| 5,957,869 A | 9/1999 | Caruso et al. | |
| 6,159,168 A | 12/2000 | Warner et al. | |

(Continued)

*Primary Examiner* — Devin B Henson
(74) *Attorney, Agent, or Firm* — Muncy, Geissler, Olds & Lowe, P.C.

(57) ABSTRACT

A portable quantification apparatus for assessing joint accessory movement is disclosed in the present invention. The apparatus includes a reference unit, a movement unit, a sliding unit and a displacement sensor. The reference unit has a first probe and a first force sensor. The movement unit has a second probe and a second force sensor. The sliding unit is disposed between the reference unit and the movement unit which allows the movement unit to slide alongside with the reference unit. When a patient is under a test, the first probe is against one of two adjacent bones of a joint, while the second probe is against the other adjacent bone. The first force sensor and the second force sensor sense a first force and a second force applying to the reference unit and the movement unit respectively. The displacement sensor measures a relative movement of the movement unit over the reference unit.

14 Claims, 12 Drawing Sheets

(56) References Cited

U.S. PATENT DOCUMENTS

| | | |
|---|---|---|
| 9,649,072 B2 | 5/2017 | Ragnarsdottir et al. |
| 2006/0052729 A1 | 3/2006 | Gurses |
| 2010/0106059 A1* | 4/2010 | Zhang .................. A61B 5/22 |
| | | 600/587 |

* cited by examiner

PORTABLE QUANTIFICATION APPARATUS AND METHOD FOR ASSESSING JOINT ACCESSORY MOVEMENT

CROSS-REFERENCE TO RELATED APPLICATIONS

This application is a continuation-in-part of co-pending U.S. application Ser. No. 14/615,973 filed Feb. 6, 2015, for which priority is claimed under 35 U.S.C. § 120; and this application claims priority of U.S. Provisional Application No. 61/936,488 filed Feb. 6, 2014 under 35 U.S.C. § 119(e); the entire contents of all of which are hereby incorporated by reference in their entirety.

FIELD OF THE INVENTION

This invention relates to a portable quantification apparatus for assessing joint accessory movement and, more particularly, to a portable quantification apparatus and method for assessing joint accessory movement by utilizing multiple probes and using one side of a joint as a reference point for further measuring the relative displacement between two bones at two sides of the joint.

BACKGROUND OF THE INVENTION

Due to insufficient physical activity, pressures from work, many people suffer from joint problems. Thus, their daily lives are affected so as to reduce the quality of life and work efficiency. Therefore, more and more people need to adopt rehabilitation treatments and request the physical therapy of the orthopedic field for recovering their daily lives.

Clinically, the decrease of the functional activities of patients is a common orthopedic problem, and the main cause comes from injured or degenerated contractile tissues, bursa or connective tissues around joints (such as articular capsule, ligaments and so on). The injuries may be resulted from fracture, ligament sprain, muscle spasm, and so on. For example, the frozen shoulder, which is very common, is resulted from the contracture of the connective tissue around the joint. Therefore, the accessory movement of the shoulder joint will be decrease and the range of motion of the patient's shoulder will be limited and so as to seriously affect the daily lives of the patient and further cause compensation to injure other body parts.

The decrease of the mobility of the spine is most often seen joint problems in clinics. The functions of the spine include providing support to the body, buffering external forces applied on the body, protecting internal organs and so on. It is comprised of, from up to down, seven cervical vertebrae, twelve thoracic vertebrae, five lumbar vertebrae, a sacrum and a coccyx to connect with the occipital bone and pelvis. There are two facet joints between adjacent spinal segments which guide and limit movement of the spinal segments. The functions of the facet joints are important but may be disrupted by degeneration, dislocation, fracture or derangement so as to cause pain and the decreased mobility of the spine. That is called "facet joint syndrome".

The manual therapy is the most effective method for treating the decreased accessory movement of the spine and other joints. The effective manual therapy should be established on an accurate assessment. The assessment of the joint accessory movement is by applying forces, which are parallel to the surface of the joint, to cause the relative movement between adjacent bones for assessing whether the joint and the tissues around the joint are normal or not. By the way, a similar maneuver also can be used for the joint mobilization. That is, different magnitudes, depths and frequencies of force are applied to relieve the patient's pain and increase the mobility of the joint. Such the treatment has a remarkable effect for treating neuromusculoskeletal pain and, more particular, for restoring the mobility of the spine. The assessment and manual therapy for joints has been performed for hundreds of years, however, its effectiveness still depends on the experience of therapists.

So far to assess the accessory movement of a joint in clinic is mainly performed by bare hands. Apparently, it is not reliable and not objective because it is difficult to control the forcing magnitude and the range of the displacement to the same extend for every assessment and different therapists would have different subjective force and displacement 'feelings/scales'. More importantly, the assessment cannot be objectively recorded for future reference, for evaluating effect of the treatment, and for discussion between therapists.

To solve this problem, there are devices of measuring the applied force and the resulting displacement of the application point, which are able to objectively quantify the 'stiffness' of the spine. However, since these devices using one probe, they cannot measurement the joint accessory movement correctly. Because the displacement of other parts of the spine, the depression of the bed, the undulation resulted from the subject's breath, etc. all will contribute to the displacement of the force application point and the one probe approach cannot eliminate these effect.

In addition, some of the devices using motors to apply force on the probe. These devices are thus big and heavy and are not convenient for practical clinical use. More importantly, these motor driven devices may make the patients feel anxious so as to cause undue muscle contraction and effect the accuracy of the assessment. Moreover, for safety concern, the forces applied by motors are limited a small range so that the condition of the joint cannot be fully assessed.

The present invention is to address the need in joint therapy and solves the problems faced by above-mentioned devices.

SUMMARY OF THE INVENTION

The present invention discloses a portable quantification apparatus for assessing joint accessory movement that measures a displacement between two adjacent bones of a joint caused by the difference of forces applied thereon. The apparatus includes a reference unit, a movement unit, a sliding unit and a displacement sensor. The reference unit has a first probe and a first force sensor. The movement unit has a second probe and a second force sensor. The sliding unit is disposed between the reference unit and the movement unit and allows the movement unit to slide alongside with the reference unit. When a patient is under a test, the first probe is against one of the two adjacent bones and the second probe is against the other one adjacent bone. The first force sensor and the second force sensor sense a first force and a second force applied to the reference unit and the movement unit respectively. The displacement sensor measures the relative movement of the movement unit over the reference unit.

The apparatus also includes an inertial measurement unit and a processing unit, wherein the inertial measurement unit is configured to detect a tilt angle of the first probe and the second probe, and the processing unit is configured to calibrate the first force, the second force and the relative movement based on the tilt angle.

In one of the embodiments of the present invention, the sliding unit further has a first sliding element and a second sliding element. The first sliding element engages with the reference unit in which the first force sensor is disposed between the first sliding element and the first probe. The second sliding element engages with the movement unit in which the second force sensor is disposed between the second sliding element and the second probe.

In another one of the embodiments of the present invention, the first sliding element is a slide rail while the second sliding element is a slider. The second sliding element slidably engages with the first sliding element so the movement unit is able to move in parallel alongside with the reference unit. Preferably, the second sliding element further has another slide rail. The movement unit is slidably placed on the slide rail so that it can move toward or away from the reference module. Preferably, the distance between the first probe and the second probe ranges substantially from 18 to 85 mm, but it is not limited to so.

In another one of the embodiments of the present invention, the displacement sensor has an optical scale and an optical encoder. Preferably, the optical scale is disposed on the reference unit and the optical encoder is disposed on the movement unit.

In another one of the embodiments of the present invention, the first force sensor and the second force sensor are both load cells.

In another one of the embodiments of the present invention, the first force sensor can be replaced by a switch and the second force sensor is a load cell.

In another one of the embodiments of the present invention, the movement unit further has a vibrating motor that serves to adjust power. After the reference module is fixed, the vibrating motor operates to cause the movement unit to apply force repeatedly for the joint therapy.

In another one of the embodiments of the present invention, the apparatus disclosed in the present invention further includes a pain index recording unit for recording a pain index whenever the patient starts feeling painful or cannot endure the pain.

In another one of the embodiments of the present invention, the apparatus disclosed in the present invention further includes an embedded system.

In another one of the embodiments of the present invention, the apparatus disclosed in the present invention further includes a reset button, a capture button and a calibration button. The reset button resets data from the optical encoder. The capture button captures the data from the first force sensor, the second force sensor, the displacement sensor module as well as the embedded system.

The features and advantages of the present invention will be understood and illustrated in the following paragraphs together with FIGS. 1-11.

BRIEF DESCRIPTION OF THE DRAWINGS

FIG. 9 (B) shows the treatment recommendations according to FIG. 9 (A).

FIG. 10 (B) shows the treatment recommendations according to FIG. 10 (A).

DETAILED DESCRIPTION OF THE INVENTION

The present invention discloses a portable quantification apparatus for assessing joint accessory movement that measures a displacement between two adjacent bones of a joint caused by the difference of forces applied thereon. Furthermore, in this regard, directional terminology, such as "up," "down," "top," "bottom," "front," "back," "left," "right," "around," "center," "horizontal," "vertical," etc., is used with reference to the orientation of the Figure(s) being described. As such, the directional terminology is used for purposes of illustration and is in no way limiting.

Figure 1:
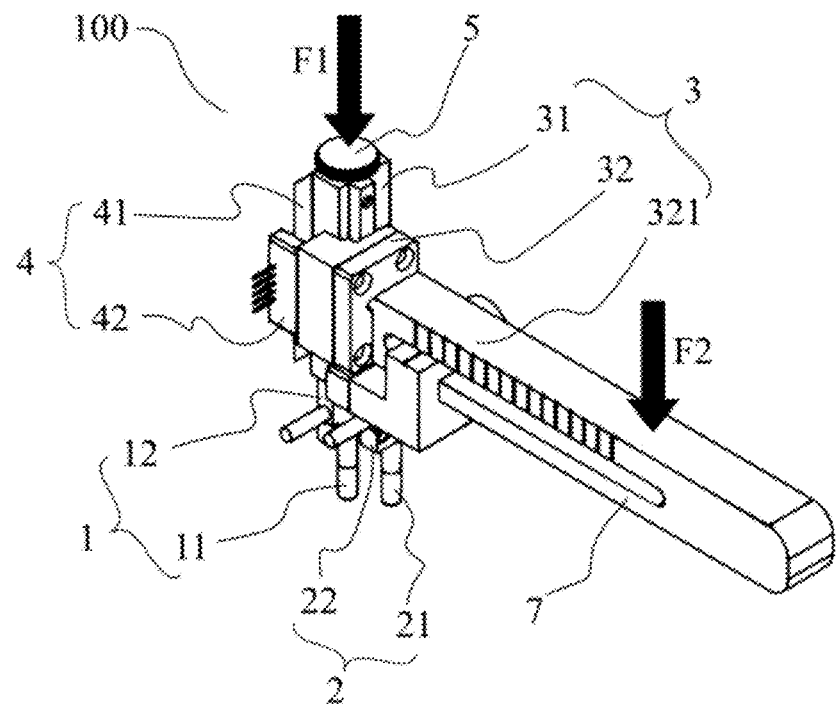
FIG. 1 is a perspective view showing a portable quantification apparatus for assessing joint accessory movement according to a preferred embodiment of the present invention.
Figure 1:
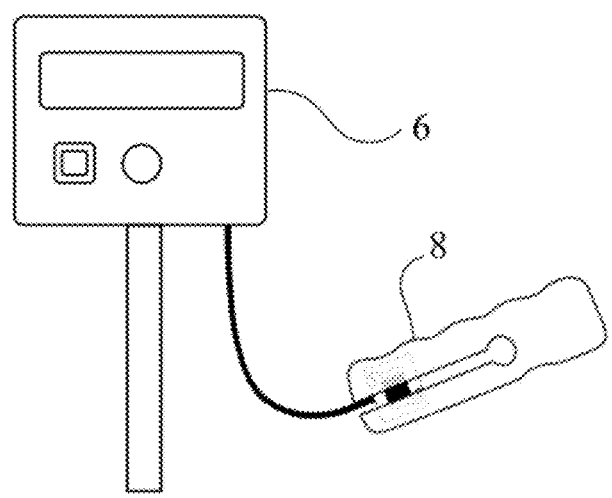
Figure 2:
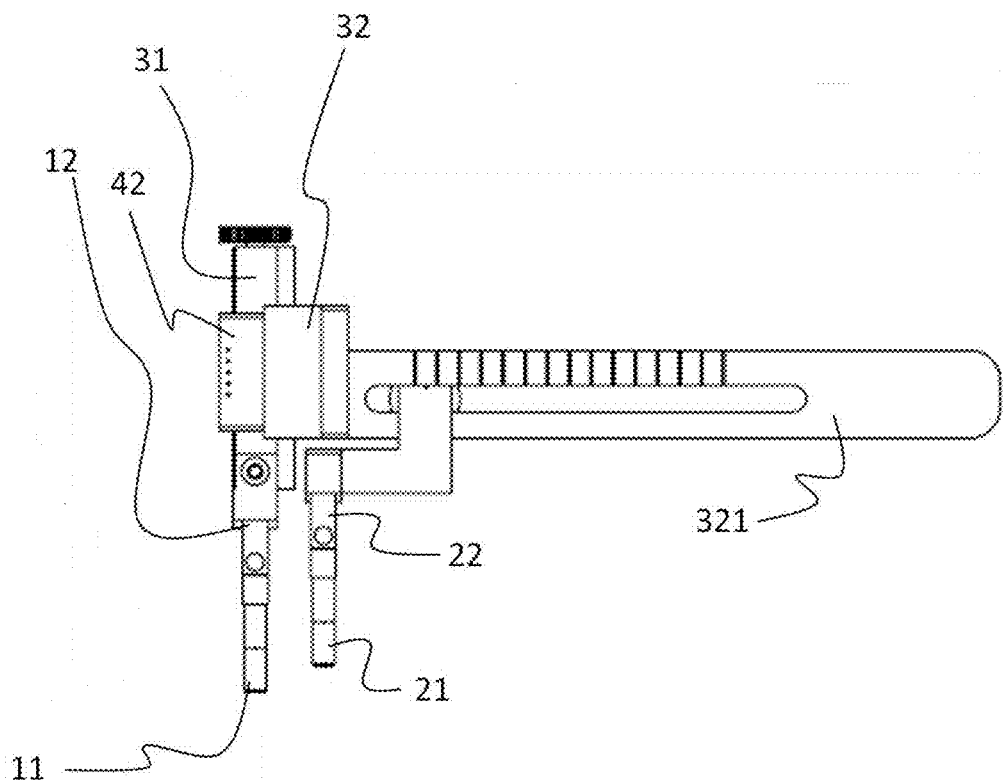
FIG. 2 is a front view showing a portable quantification apparatus for assessing joint accessory movement according to a preferred embodiment of the present invention.

To better understand the concept surrounding the present invention, FIG. 1 is referred to in conjunction with FIG. 2. FIG. 1 is a perspective view showing a portable quantification apparatus for assessing joint accessory movement according to a preferred embodiment of the present invention. FIG. 2 is a front view of the portable quantification apparatus. As can be seen from FIGS. 1 and 2, the apparatus 100 includes a reference unit 1, a movement unit 2, a sliding unit 3, a displacement sensor 4, an inertial measurement unit 5 and a processing unit 6. The reference unit 1 has a first probe 11 and a first force sensor 12. The movement unit 2 has a second probe 21 and a second force sensor 22. In a preferred embodiment, the first force sensor 12 and the second force sensor 22 are both load cells. In another preferred embodiment, the first force sensor 12 is a switch and the second force sensor 22 is a load cell, but they are not limited to so. By the settings of the two force sensors, the measurement positions of the reference unit 1 and the movement unit 2 may be switch to exam whether the tension is affected by the upper or lower levels of joints. Furthermore, in the event where a continuous measurement on different joints is desired, the apparatus can automatically stop recording measurement data when the probe 11 of the reference unit 1 is removed from the subject and start recording a new measurement data when the probe 11 of the reference unit 1 contacts the other joint of the subject. Therefore, the function can be quickly switched to meet the clinical need.

Inertial measurement unit 5 may be an accelerometer or other units capable of sensing tilted angles. Processing unit 6 may include one or more processors, microprocessors, or other devices capable of data processing and operating. Preferably, the processing unit 6 includes an embedded system chip and a communication chip.

The sliding unit 3 is disposed between the reference unit 1 and the movement unit 2 which allows the movement unit 2 to be able to slide alongside with the reference unit 1. In particular, in the preferred embodiment, the sliding unit 3 has a first sliding element 31 and a second sliding element 32. The first sliding element 31 engages with the reference unit 1 in which the first force sensor 12 is disposed between the first sliding element 31 and the first probe 11. When a patient is under a test, a first force F1 is applied to the reference unit 1 through the first sliding element 31. The first force sensor 12 then measures the first force F1, i.e. the force that applies to one of the adjacent bone contacting with the first probe 11. The second sliding element 32 engages with the movement unit 2 in which the second force sensor 22 is disposed between the second sliding element 32 and the second probe 21. The second force sensor 22 measures the second force F2 that applies to the other adjacent bone. Not only the first and the second forces F1 and F2 are measured, the difference between the two is also obtained by the above arrangement of the apparatus 100.

Furthermore, in another preferred embodiment of the present invention, the first sliding element 31 is a slide rail and the second sliding element 32 is a slider. The second sliding element 32 slidably engages with the first sliding element 31. As such, the movement unit 2 is able to move in parallel alongside with the reference unit 1. It is not intended to be a limitation limit in the present invention, the distance of movement made by the movement unit 2 is preferably about 30 mm.

In addition, the second sliding element 32 further includes another slide rail 321. The movement unit 2 is slidably placed on the slide rail 321. The movement unit 2 is able to move toward or away from the reference unit 1 through the slide rail 321 so as to adjust the distance between the first probe 11 and the second probe 21 according to the size of the joint subject to test. Preferably, the distance between the first probe 11 and the second probe 21 ranges from 18 to 85 mm though it is not limited by the present invention. Moreover, the horizontal slide rail 321 may also serve as a handle for the portable quantification apparatus for assessing joint accessory movement disclosed in the present invention. After fixing the distance between the first probe 11 and the second probe 21, a therapist may further apply the second force F2 to the horizontal slide rail 321 to cause the movement unit 2 to move in parallel alongside with the reference unit 1. The operation will be further described in the following paragraphs.

As can be seen in FIG. 1, the displacement sensor 4 includes an optical scale 41 and an optical encoder 42. Preferably, the optical scale 41 is disposed on the reference unit 1 while the optical encoder 42 is disposed on the movement unit 2. The optical scale 41 and the optical encoder 42 serve to measure the relative movement of the movement unit 2 over the reference unit 1. The relative movement results from the difference of forces applied to the two adjacent bones of the joint.

Figure 3A:
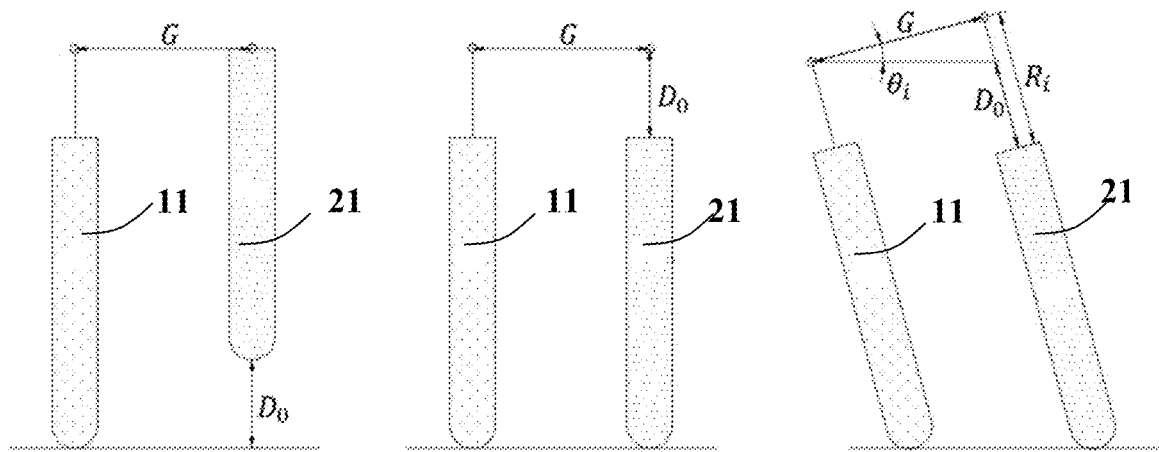
FIG. 3(A) and FIG. 3(B) are the schematic diagrams showing the probe's tilt during measurement and the steps to calibrate sensors and get system parameters.
Figure 3B:
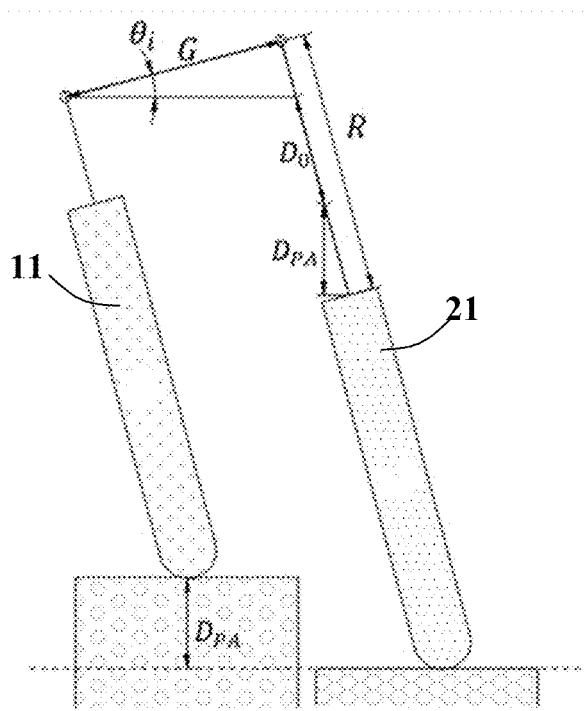

Please refer to FIG. 3 (A) and FIG. 3 (B). If the therapist fails to apply the force vertically or any tilting has occurred when applying the force, the first probe 11 and the second probe 21 will not be vertically positioned on the joint bones subject to the measurement. That is, the obtained force and relative movement will not be in the vertical direction. Thus, it is necessary to measure the tilted angle by the inertial measurement unit 5, and calculate the component in the vertical direction to calibrate the first force, the second force and the relative movement. FIG. 3 (A) shows the steps to calibrate the sensors and obtain system parameters $D_0$ and G. The related calculation is described as follows:

$$R_i + G \tan \theta_i + D_0 \qquad (1)$$

$$D_{PA} = (R - D_0 - G \tan \theta) \cos \theta \qquad (2)$$

$$F_{PA} = F \cos \theta \qquad (3)$$

G: the gap distance between probes obtained from calibration
$D_0$: the distance in the level surface obtained from calibration
θ: the tilting angle
$D_{PA}$: the posterior-anterior displacement
R: the encoder reading
F: the total force applied
$F_{PA}$: the posterior-anterior direction force Before the measurement, the therapist should execute the calibration procedure to calibrate the sensors and obtain the system parameters, which was activated by calibration button on the apparatus or first starting up the system. The therapist firstly lifted the apparatus in the air to obtain the offsets of the force sensor (for example, the load cell) and the origin of the displacement sensor (for example, the optical encoder). Secondly, the therapist place the apparatus on a hard level surface, e.g. a bench table, and aligned the bubble level indicator on the apparatus to ensure the probes were vertical to obtain the misalignment of the inertial measurement unit (for example, the accelerometer) and the level offset $D_0$ from encoder reading. Thirdly, the apparatus was tilted in all directions to a couple of tens degrees to get serial angles $\theta_i$ and related encoder reading $R_i$. As shown in FIG. 3 (A), the gap distance G could be calculated by the serial $\theta_i$ and $R_i$ with least square linear regression as shown in equation (1).

As shown in FIG. 3 (A), the tilt of the apparatus could induce extra encoder readings without actual displacement between contact points. In addition, as depicted in FIG. 3 (B), when the contact points would be not on the same level, i.e. performing measurement, the posterior-anterior component displacement could be calculated by the equation (2). Similarly, the posterior-anterior component of the applying force could be calculated by the equation (3).

Figure 4:
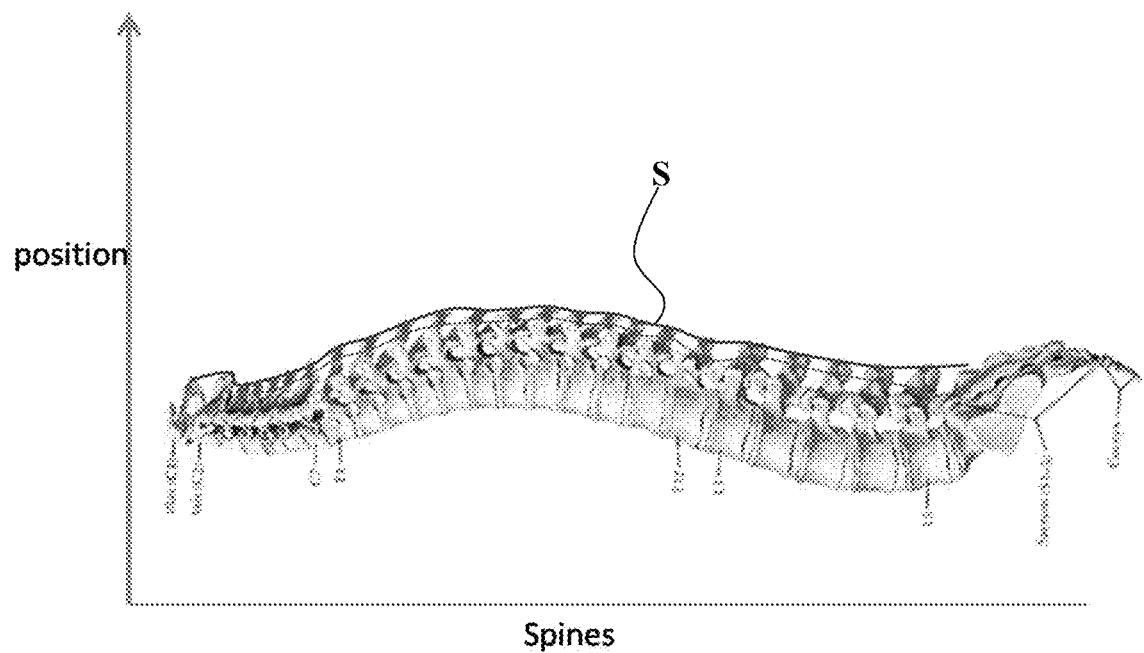
FIG. 4 shows a relative position diagrams and a spinal curve S obtained by the present invention.

Through the above-mentioned calibration, the displacement in the posterior-anterior direction can be calculated. Based on the measured initial spinal joints vertical offset of the subject, the spinal curve S can be profiled (as shown in FIG. 4). Besides, the individual joint property can be marked in corresponded joint for the therapists' reference for diagnosis or treatment.

In an embodiment, the apparatus 100 further includes a gyroscope device 5. The gyroscope device 5 generates a gyro effect to reduce the high frequency tilting caused by the therapist when applying the force and therefore further stabilize the measurement.

The present invention uses an inertial measurement unit and/or a gyro device for stabilization. When measuring, the probe is in contact with the subject without any supporting frame. Therefore, the portability is enhanced as well.

It is noteworthy that therapists may perform a joint mobilization by using the apparatus disclosed in the present invention. That is, after fixing the first probe 11, a therapist may force the handle (i.e. the horizontal slide rail 321) repeatedly to cause the second probe 21 to move forward and backward accordingly. By doing so, the joint is therefore eased. As such, the movement unit 2 may preferably further include a vibrating motor (whose power is adjustable) to apply forces repeatedly.

In the preferred embodiment, the apparatus of the present invention may further include a pain index recording unit 8, an embedded system, a transmitter, and a user interface (not shown in the figures). Whenever a patient starts feeling painful or cannot endure the pain, he or she may press a recording button. The pain index recording unit 8 then records the timing and/or an index of pain for therapists' later reference.

The embedded system integrates data from the first force sensor 12, the second force sensor 22, and the displacement sensor 4, the inertial measurement unit 5 and the pain index recording unit. The data may be further analyzed for later study. Additionally, the user interface preferably equips with a liquid crystal display and/or buttons for therapists' convenience to use and also serves to give notices, such as speeds of applied forces, displacement of joint (i.e. start point and end point), and alerts of pain suffered by the patient. The user interface may also provide real time information about the position of the movement unit in light of the magnitude of the applied force. Such information is helpful for therapists to understand the way in which the force should be applied to the two adjacent bones of the joint. Furthermore, the data can be stored for therapists' later reference.

Figure 5:
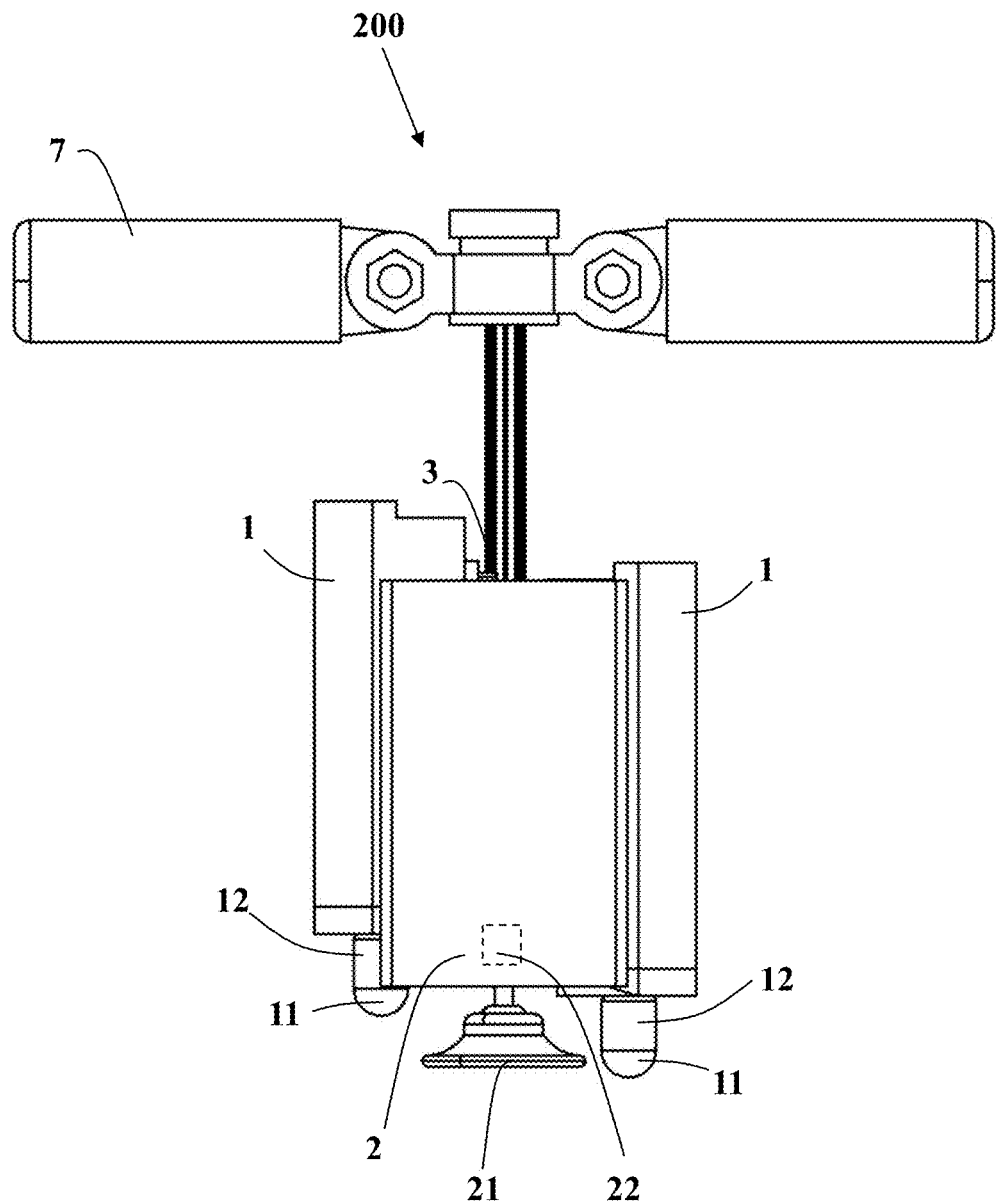
FIG. 5 shows a lateral view of another embodiment of the apparatus according to the present invention.
Figure 6:
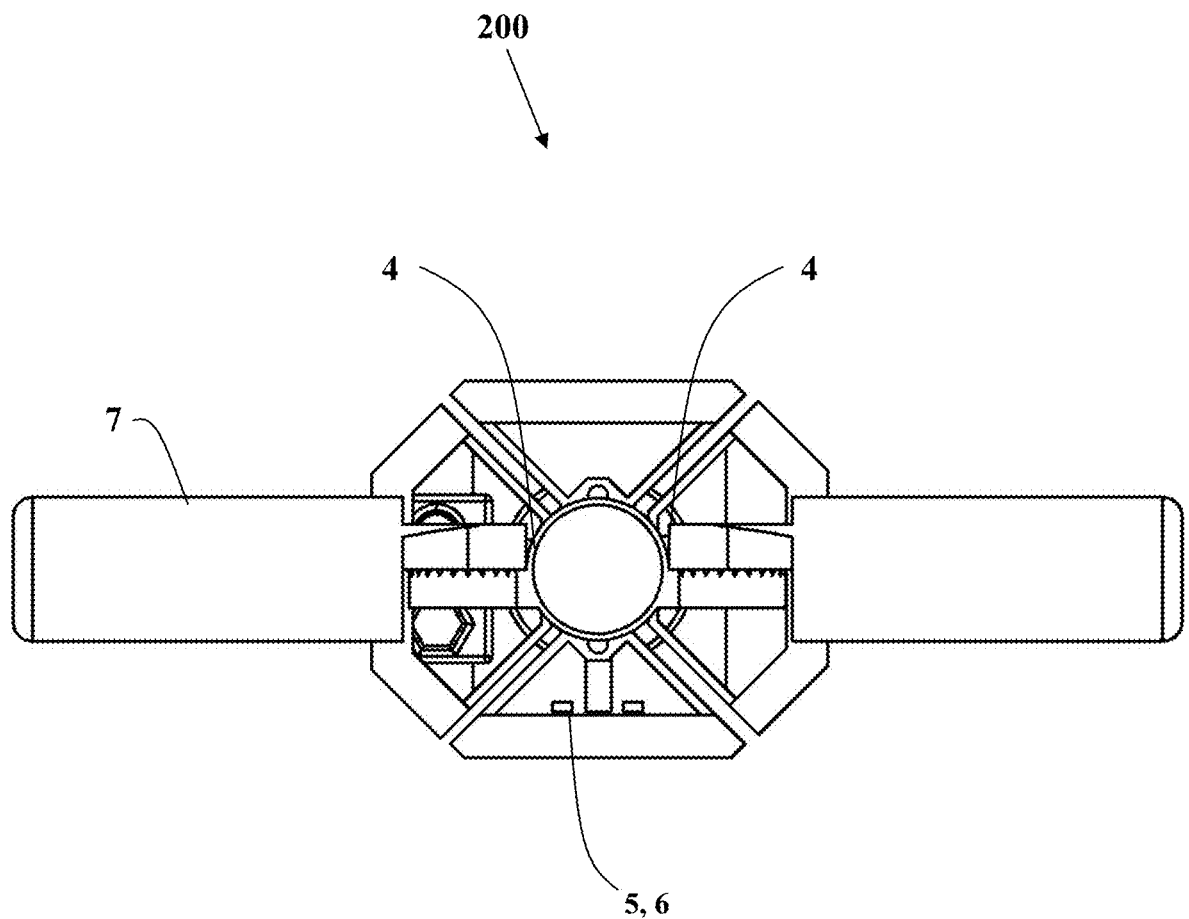
FIG. 6 shows a top view of another embodiment of the apparatus according to the present invention.
Figure 7:
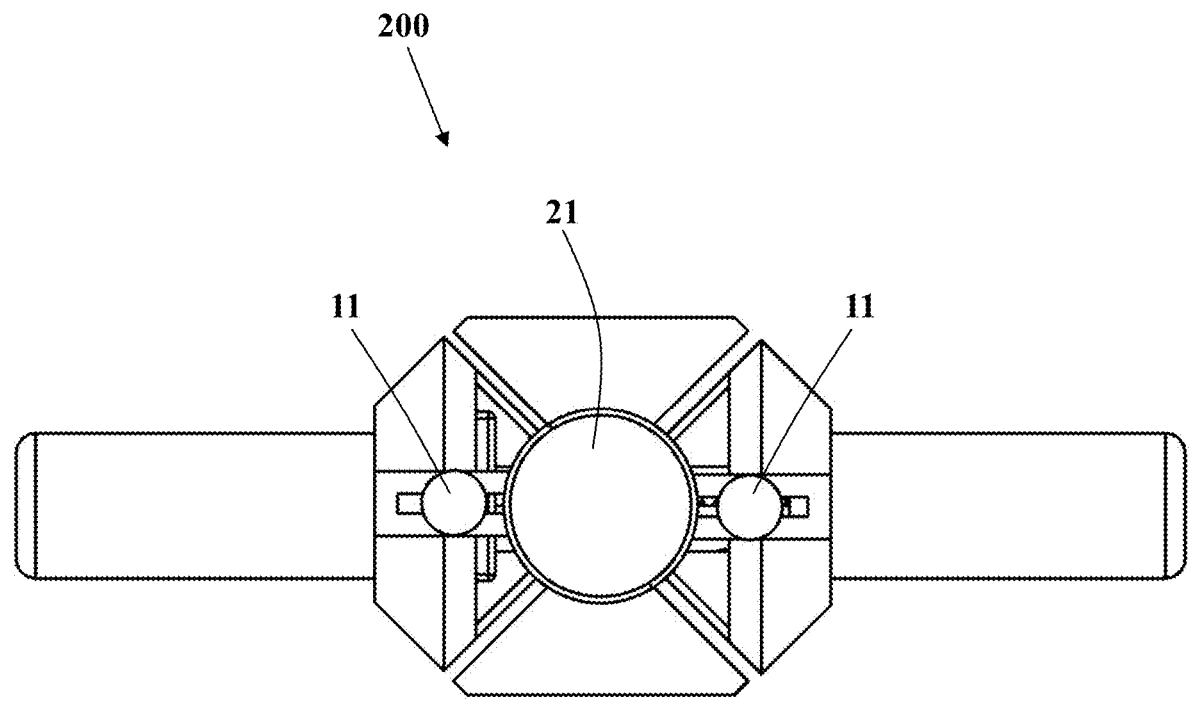
FIG. 7 shows a bottom view of another embodiment of the apparatus according to the present invention.

FIG. 5 and FIG. 6 are another embodiment of the present invention. The apparatus 200 may include at least two reference units 1, each includes a probe 11 and a force sensor 12. The movement unit 2 located between the two reference units 1. The reference units 1 and the movement unit 2 are respectively provided with a sliding unit 3, so that the movement unit 2 can move toward to the two reference units 1. Additionally, there are two displacement sensors 4 provided for measuring the relative movement between the two reference units 1 and the movement units 2.

In this embodiment, a heavy item (for example, the shell or weights) can be put on the two reference units as the exerting force. Under such a design, the two reference units 1 can be used to simultaneously measure the influence of the displacement between the previous section and the next section of the spine. When measuring, the probe 11 of the two reference units 1 contacts the frontal and the distal bones of the two joints, and the probe 21 of the movement unit 2 contacts the middle bones. The therapist then applies a force to the movement unit 2 via the handle 7. The force sensor 22 of the movement unit 2 measures the force applied by the probe 21 to the bones. Thus, it will be able to know the difference between the forces applied to the two reference units 1 and the movement unit 2, and meanwhile obtain the relative movement of such. Similarly, the inertial sensor 5 measures the tilted angle, and the processing unit 6 calculates the component in the vertical direction to calibrate the force and the relative movement.

Please refer to FIG. 5 and FIG. 6. In the above embodiments, the distance between the probe 11 of the two reference units 1 and the probe 21 of the movement unit 2 is adjustable by, for example, a sliding rail. The distance is about 10 to 30 mm. In addition, the handle 7 is rotatable like a ratchet, which allows the therapist to operate more easily.

Figure 8:
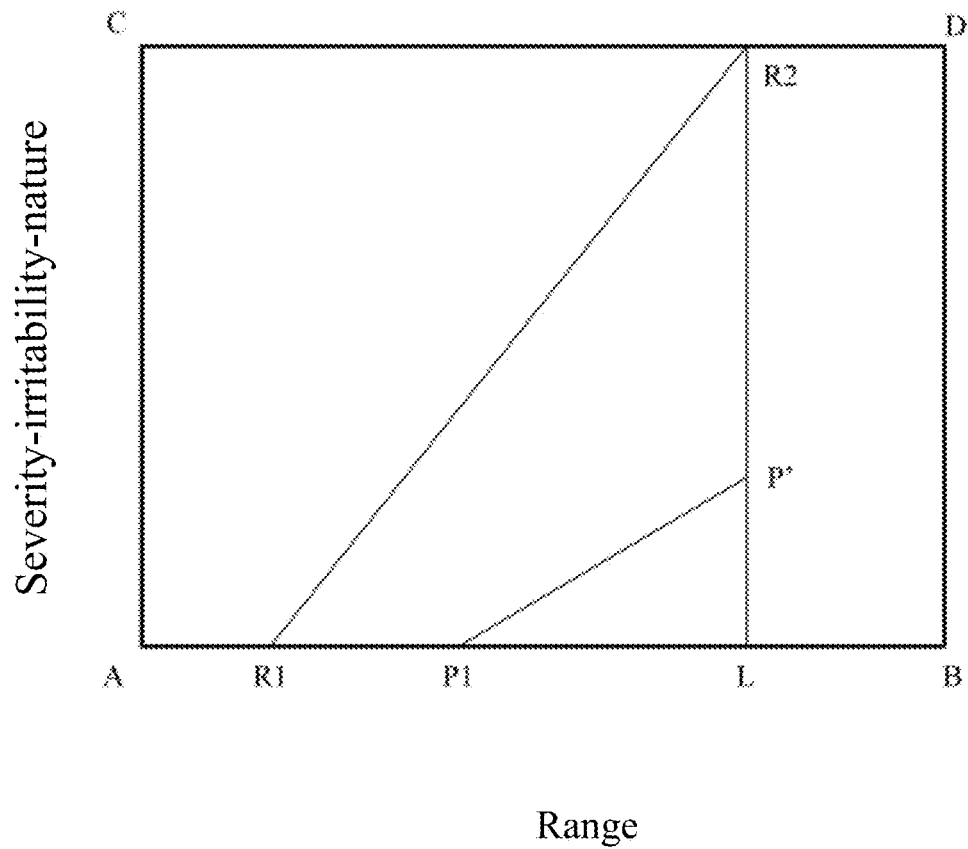
FIG. 8, which shows the movement diagram of prior art.

Please refer to FIG. 8, which shows the known movement diagram of prior art. The movement diagrams are a tool used to aid teaching and communication, i.e. an objective means of quantifying the relationship between movement and pain determined during a passive examination technique. The components considered in a movement diagram pain, spasm-free resistance (stiffness), muscle spasm (where spasm is referring to protective muscle spasm secondary to joint disorder, not spasticity caused by upper neurone disease and not voluntary contraction of muscles). The steps of movement diagram construction comprising: (1) Start off by drawing a box. (2) Mark the horizontal line AB=which represents the range of movement, where A to B is the limit of normal passive movement. (ROM is determined to be normal if an overpressure can be applied at the end of range without pain, and is denoted by a double tick in clinical notes). (3) Mark the vertical line AC=which represents the quality, nature, or intensity of the variables being plotted. Mark P1=the first point of pain along the AB Line. Mark R1=the first point of resistance along the AB line. (4) Determine the limiting factor (Pain or resistance) and at which point through range the limit occurs. At this point draw a vertical line and label L with a description of the limiting factor i.e. determine what L represents. (5) Determine the behaviour of P1P2 and R1R2 and plot them in the box to create linear lines or curved lines.

Traditionally, movement diagrams are profiled heavily based on therapists' experience. Alternatively, the device such as the one disclosed in U.S. Pat. No. 9,649,072B2 may be adopted. However, neither of the traditional methods considers whether the direction of the force applied by the therapist is vertical or the relative movement caused by the swaying when the force is applied. Thus, the traditional methods cannot provide the data of the force and relative movement in vertical direction.

Figure 9:
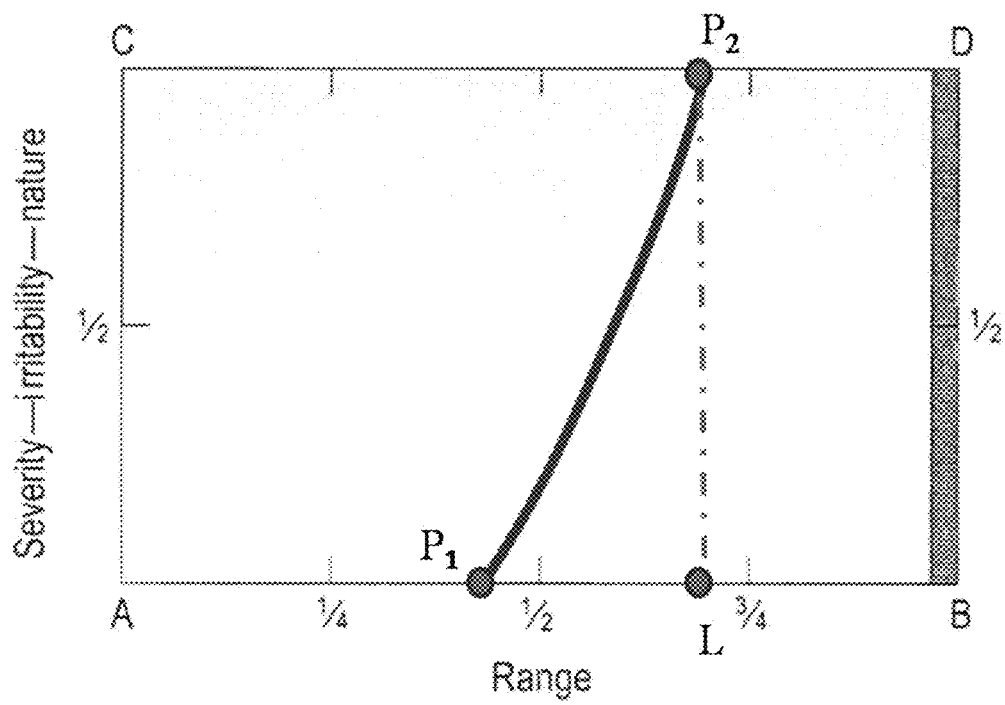
FIG. 9 (A) is a movement diagram obtained by repeated measurements of the same joint by the present invention.
Figure 9:
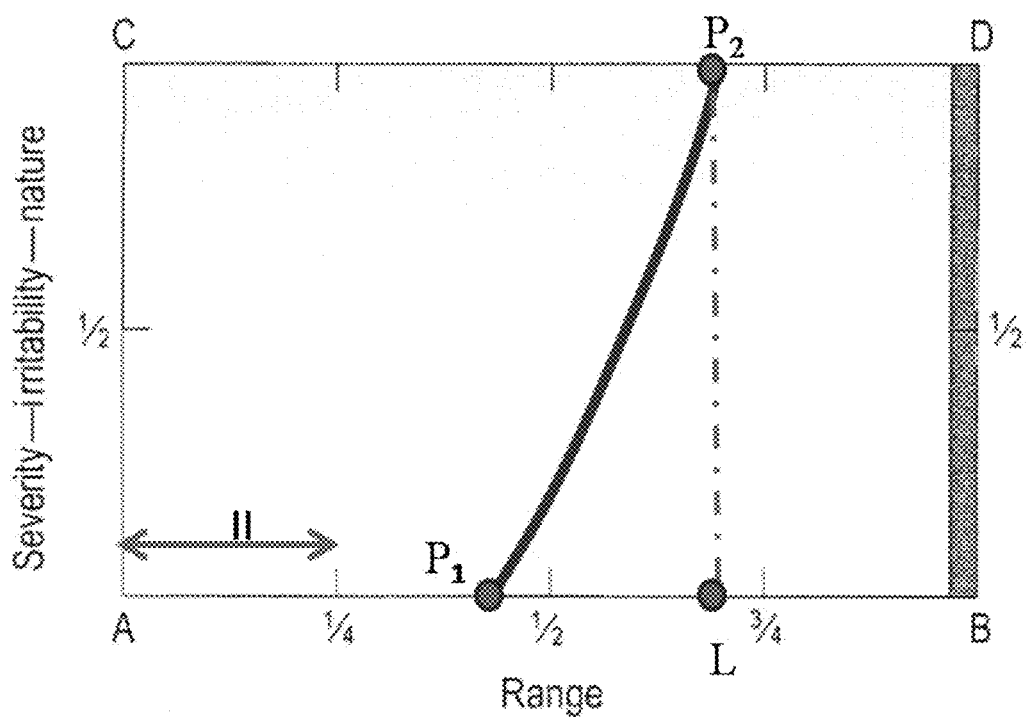

FIG. 9 (A) is a movement diagram obtained from measuring the same joint of the subject repeatedly through the apparatus provided in the present invention. In FIG. 9, $P_1$-$P_2$ is a curved line showing the degree of pain. Based on the data shown in FIG. 9 (A), it can be obtained that the subject is suffering from limited joint activity due to pain. A treatment recommendation is as shown in FIG. 9 (B). The subject will be giving a large amplitude movement slowly within a painless range (II).

Please refer to FIG. 10(A), which is a diagram of another movement diagram obtained from measuring the same joint of the subject repeatedly through the apparatus provided in the present invention. As illustrated, $R_1$-$R_2$ is a curved line showing the degree of resistance. From the date, the restricted state of the subject's joints can be known. Based on FIG. 10(A), a treatment recommendation can be given as shown in FIG. 10(B). Thus, the subject is giving a small amplitude movement rapidly at the restricted position (IV++).

Figure 10:
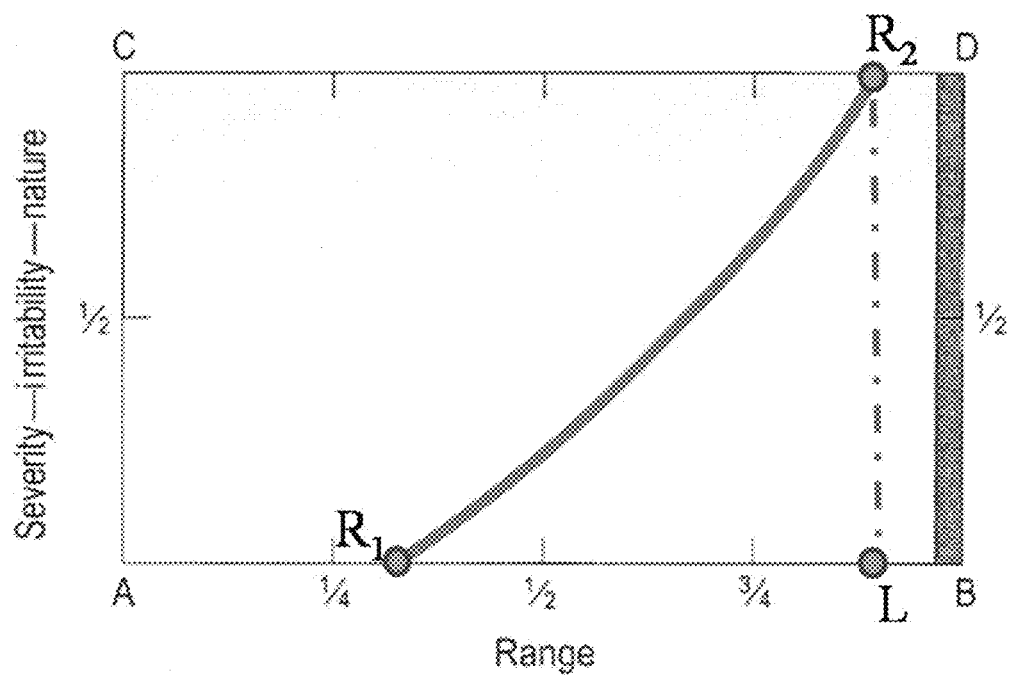
FIG. 10 (A) is another movement diagram obtained by repeated measurements of the same joint by the present invention.
Figure 10:
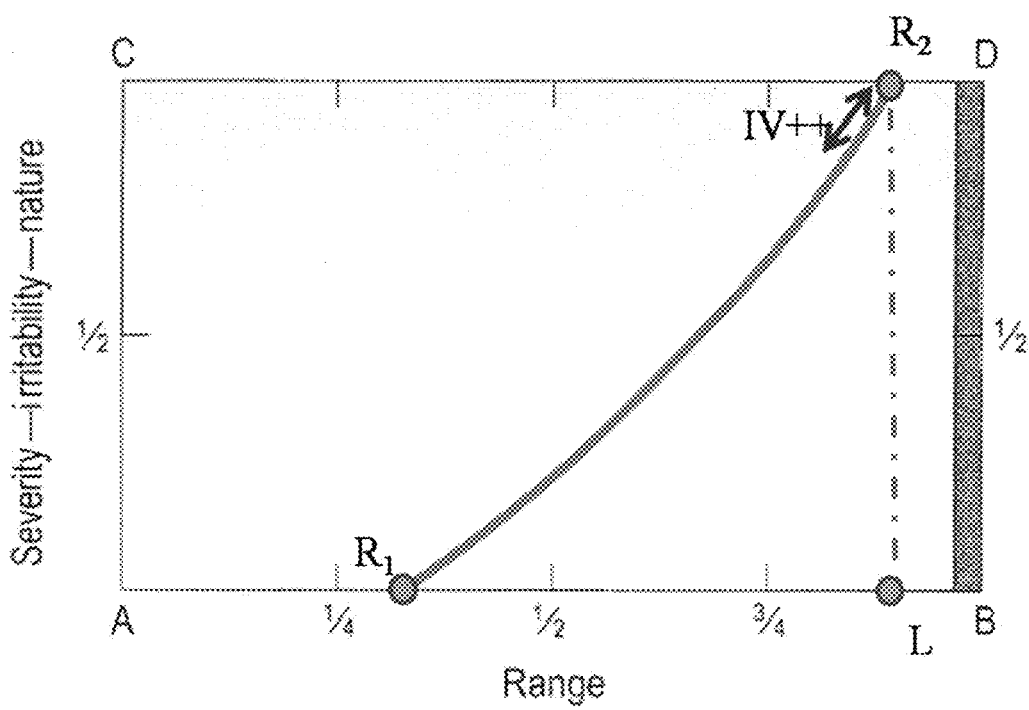

When the conditions of FIG. 9 (A) and FIG. 10 (A) occur at the same time, a large amplitude movement slowly within a painless range is firstly applied. After a while, the motion is retested. If it is determined that the pain is not the cause for the limit, the apparatus presses to the position subject to the limit and applies a small amplitude movement rapidly at the restricted position.

The treatment prescription given by the above movement diagram can also be achieved by a vibration motor. For example, when the joint is under pressure to the treatment area, the motor will be automatically activated for treatment and instantly displayed on the man-machine interface with the magnitude and range of force applied during treatment. The data, movement diagram and treatment prescription obtained by the device can be displayed and stored on the display of the user interface as well as displayed on a mobile phone or a computer.

Preferably, the apparatus disclosed in the present invention may further include a reset button, a capture button and a calibration button (not shown in the figures). When the reset button is pushed, the optical encoder 42 is set as zero displacement. While the capture button is pressed, the data from the first force sensor 11, the second force sensor 21, the displacement sensor 4, the inertial measurement unit 5, as well as other sensors will be recorded. The reset button and the capture button may be integrated in the user interface; but it is not limited to so.

The operation of the portable quantification apparatus disclosed in the present invention will be discussed in further detail below. Firstly, before a test begins, the first force F1 that applies to the first probe 11 must be adjusted. In more particular, the magnitude of the first force F1 must be able to press the first probe 11 close to the bone in order to reduce the impact resulted from soft tissues. Such magnitude is then fixed so it will not be changed due to the movement unit 2. To obtain a proper magnitude of the first force F1, a rigidity test of soft tissue can be performed against the non-joint apophysis of the patient. In detail, making the second probe 21 contact with the skin without applying extra force; subsequently gradually increasing a reference weight that put on the reference unit 1 until the displacement does not substantially change. At this moment, the hard portion of the bone is contacted. The minimum threshold value of the reference weight is thereafter adopted as the first force F1.

Figure 11:
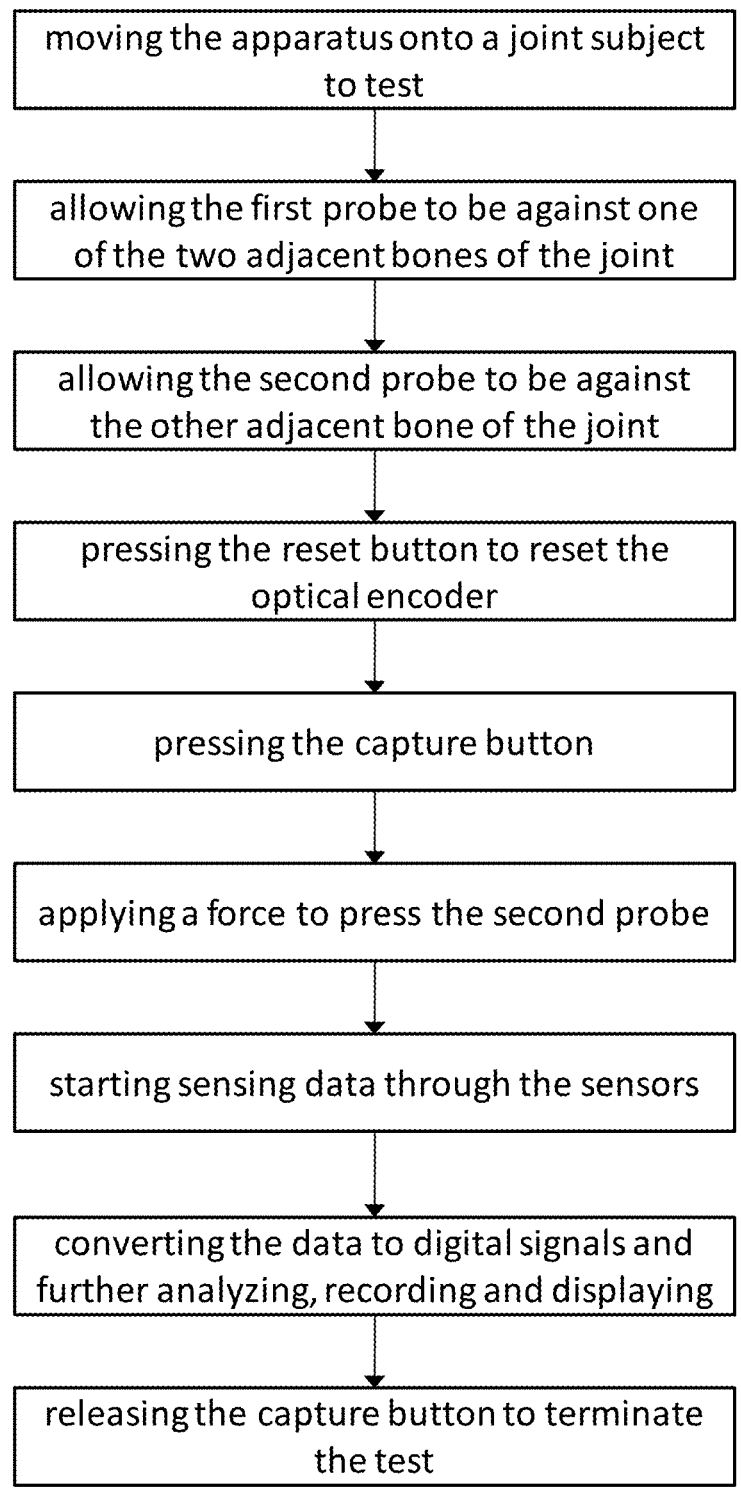
FIG. 11 is a flow chart of operating a portable quantification apparatus for assessing joint accessory movement according to a preferred embodiment of the present invention.

Please refer to FIG. 11, when the apparatus 100 is moved onto a joint subject to test, the first probe 11 is against one of the two adjacent bones of the joint, while the second probe 12 is against the other adjacent bone. Pressing the reset button to reset the optical encoder 42 and then pressing the capture button. The second probe 21 is also pressed. All the sensors in the apparatus 100, such as the first force sensor 12, the second force sensor 22, the optical scale 41, the optical encoder 42, etc. start sensing data. The then obtained data is converted to digital signals through the embedded system for further calibrating, analysis, recording and display. Finally, releasing the capture button to terminate the test; a result is therefore obtained.

Figure 12:
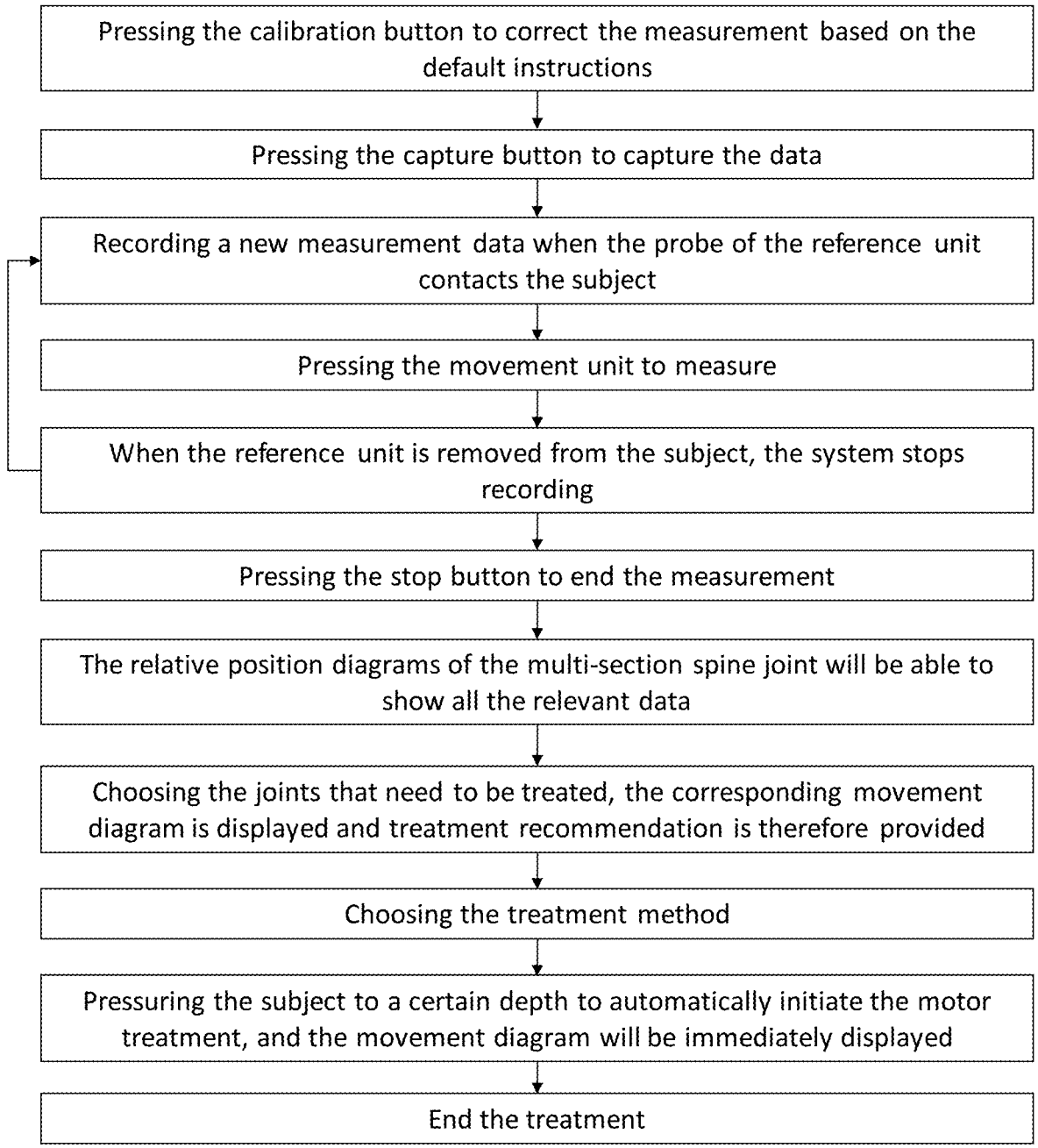
FIG. 12 is a flow chart of operating the apparatus for assessing the joint accessory movement and patient treatments according to a preferred embodiment of the present invention.

FIG. 12 shows how the present invention can be used for both measurement and treatment. The calibration button is pressed to correct the measurement based on the default instructions, and then the capture button is pressured to capture the data. The same apparatus is on the two ends of the joint subject to measurement; one end is touched by the first probe and the other is by the second probe. When the probe of the reference unit contacts the subject, a new measurement data is recorded. The therapist starts to press the movement unit to measure. The degree of force, the relative movement, the pain index records, and other relevant information can be displayed in real-time on a screen. When the reference unit is removed from the subject, the system stops recording. The stop button is then pressed to end the measurement.

Afterward, the relative position diagrams of the multi-section spine joint will be able to show all the relevant data. Based on that, the therapist can choose the joints that need to be treated. Once selected, the corresponding movement diagram is displayed and treatment prescription is therefore provided. Next, the therapist can choose the treatment method and pressure the subject to a certain depth to automatically initiate the motor treatment. The movement diagram will be immediately displayed. As a result, the therapist is able to instantly understand the effect of treatment. At the last step, end the treatment.

Based upon the above, if the apparatus 100 of the present invention is applied to spine joints, an adjoined vertebra is taken as a reference point for measuring displacement between the adjoined vertebrae. The two probes are placed across a joint. That is, one of the probes serves as a reference end and the other serves as a movement end. The accessory movement of the joint is therefore obtained by the result of the difference of the forces applied to the two ends. As such, therapists are benefited from the present invention. They are able to objectively quantify joint accessory movements by measuring displacements between the two adjacent bones based upon the above mentioned operation. Additionally, pain induced during assessment is also useful as far as clinical concern. The present invention may also serve as tools for the sake of therapist training. To sum up, the advantages of the present invention are as follows: (1) the apparatus is capable of objectively quantifying the forces applied to the two sides of a joint and displacement resulted from it; (2) the distance between the two probes can be adjusted according to the size of the joint subject to test; (3) the confidence level for the manual assessment of the joint accessory movement is increased; (4) the apparatus further assists therapists to better communicate and understand patients' condition; based upon which, therapists are able to pass on the clinical experience; (5) the apparatus provides quantificational notifications during test which may increase the accuracy of the treatment; (6) the apparatus may also analyze how successful the treatment is after the treatment is completed so as to increase the confidence level of the treatment; (7) the apparatus is portable for clinical use; and (8) therapists can learn the joint mobilization technique through the apparatus disclosed herein.

Although the present invention has been described in considerable detail with reference to certain preferred embodiments thereof, the disclosure is not for limiting the scope of the invention. Persons having ordinary skill in the art may make various modifications and changes without departing from the scope and spirit of the invention. Therefore, the scope of the appended claims should not be limited to the description of the preferred embodiments described above.

What is claimed is:

1. A portable quantification apparatus for assessing joint accessory movement that measures a displacement caused by the difference of forces applied to two adjacent bones of a joint of a subject, comprising:

a reference unit having a first probe and a first force sensor;

a movement unit having a second probe and a second force sensor; wherein only the reference unit and the movement unit are removably contacted with the joint of the subject;

a sliding unit is disposed between the reference unit and the movement unit and slides alongside with the reference unit; and a displacement sensor;

an inertial measurement unit configured to measure a tilt angle of the first probe and the second probe;

a processing unit calculating a component in a direction to calibrate a first force, a second force and a relative movement;

wherein the first probe is against one of the adjacent bones while the second probe is against the other bone; the first force sensor and the second force sensor sense the first force and the second force applied to the reference unit and the movement unit respectively, and the displacement sensor measures the relative movement of the movement unit over the reference unit, wherein the processing unit is configured to calibrate the tilt angle, the first force, the second force and the relative movement, and based on the tilt angle to calculate the component of the first force, the second force, and the displacement.

2. The apparatus according to claim 1, wherein the sliding unit comprises a first sliding element engaging with the reference unit and a second sliding element engaging with the movement unit in which the first force sensor is disposed between the first sliding element and the first probe and the second force sensor is disposed between the second sliding element and the second probe.

3. The apparatus according to claim 2, wherein the second sliding element slidably engages with the first sliding element and the movement unit moves in parallel alongside with the reference unit.

4. The apparatus according to claim 3, wherein the first sliding element is a slide rail while the second sliding element is a slider.

5. The apparatus according to claim 3, wherein the second sliding element further comprises a slide rail; the movement unit is slidably placed on the slide rail and moves toward and away from the reference unit.

6. The apparatus according to claim 1, wherein the displacement sensor comprises an optical scale disposed on the reference unit and an optical encoder disposed on the movement unit.

7. The apparatus according to claim 1, wherein the first force sensor and the second force sensor are load cells.

8. The apparatus according to claim 1, wherein the first force sensor is a switch and the second force sensor is a load cell.

9. The apparatus according to claim 1, wherein the movement unit further comprises a vibrating motor whose power is adjustable; the vibrating motor applies force repeatedly to the movement unit for joint therapies.

10. The apparatus according to claim 1, wherein the apparatus further comprising a pain index recording unit that records pain index whenever a patient starts feeling painful or cannot endure the pain, wherein the processing unit combines the first force, second force and the relative movement to obtain a movement diagram.

11. The apparatus according to claim 1, wherein the processing unit includes an embedded system chip and a communication chip.

12. The apparatus according to claim 1, wherein the apparatus further comprising a gyroscope device, wherein the gyroscope device generating a gyro effect to reduce the tilt angle and stabilize the apparatus.

13. A method for quantifying joint accessory movement that measures a displacement caused by the difference of forces applied to two adjacent bones of a joint, comprising:
(A) providing an apparatus of claim 1;
(B) loading the first probe of reference unit to a subject's reference bone side of joint, and loading the second probe of movement unit to a subject's movement bone side of joint;
(C) pressing the movement unit to obtain the relative movement, the first force and the second force;
(D) recording a pain index of subject;
(E) correcting the first force, second force and relative movement based on the tilt angle;
(F) repeating steps (C), (D) and (E), combining the first force, the second force, the relative movement and the pain index to obtain a movement diagram; and
(G) giving treatment recommendations based on the movement diagram.

14. The method according to claim 13, wherein the method further comprising:
(H1) determining whether a joint activity of subject is limited due to pain, if so, giving an amplitude movement within a painless range.

* * * * *